US00PP13107P2

(12) United States Plant Patent
Carruth

(10) Patent No.: US PP13,107 P3
(45) Date of Patent: Oct. 22, 2002

(54) CLIMBING ROSE PLANT NAMED 'WEKSAMSOU'

(75) Inventor: Thomas F. Carruth, Altadena, CA (US)

(73) Assignee: Weeks Wholesale Rose Grower, Inc., Upland, CA (US)

( * ) Notice: Subject to any disclaimer, the term of this patent is extended or adjusted under 35 U.S.C. 154(b) by 0 days.

(21) Appl. No.: 09/754,413

(22) Filed: Jan. 2, 2001

(65) Prior Publication Data

US 2002/0088030 P1 Jul. 4, 2002

(51) Int. Cl.[7] ..... A01H 5/00
(52) U.S. Cl. ..... Plt./115
(58) Field of Search ..... Plt./115

*Primary Examiner*—Bruce R. Campell
*Assistant Examiner*—Susan B. McCormick
(74) *Attorney, Agent, or Firm*—Christie, Parker & Hale, LLP

(57) ABSTRACT

A new variety of Climbing rose suitable for garden decoration, having flowers of even medium red coloration.

1 Drawing Sheet

BOTANICAL CLASSIFICATION

*Rosa hybrida.*

VARIETY DENOMINATION

'Weksamsou'.

BACKGROUND OF THE INVENTION

This invention relates to a new and distinct variety of Climbing Rose. The varietal denomination of the new variety is *Rosa hybrida* cv. 'WEKsamsou'. It has as its seed parent the variety known as 'Don Juan' (U.S. Plant Pat. No. 1,864) and as its pollen parent an undistributed seedling of my creation.

SUMMARY OF THE INVENTION

Among the features which distinguish the new variety from other presently available and commercial rose cultivars known to the inventor are the following combination of characteristics: its numerous hairs on the rachis upper side, its globular bud shape, its even red coloration and its large clusters. The plant has a climbing growth habit, suitable for garden decoration.

Asexual reproduction of the new variety by budding as performed in Kern County and Upland, Calif., shows that the foregoing and other distinguishing characteristics come true to form and are established and transmitted through succeeding propagations. 'WEKsamsou' may be asexually propagated by cuttings, budding and grafting.

COMPARISON WITH PARENTS

The new rose may be distinguished from its seed parent, 'Don Juan' by the following combination of characteristics: whereas 'WEKsamsou' bears medium size flowers of even medium red coloration, 'Don Juan' bears significantly larger flowers of darker red coloration with some black pigmentation on the outermost petals. The new variety bears its flowers in large clusters, whereas the seed parent bears its flowers in significantly smaller clusters.

The new variety may be distinguished from its pollen parent, an undisseminated seedling of my creation, by the following combination of characteristics: whereas 'WEKsamsou' bears flowers of even medium red coloration with very double petalage (about 36 to 50 petals), the pollen parent bears flowers of brighter red coloration with significantly lower petalage (about 5 to about 10). The new variety bears matte to slightly semi-glossy foliage, whereas the pollen parent bears very glossy foliage.

BRIEF DESCRIPTION OF ILLUSTRATION

The accompanying photograph illustrates 3 to 4 year old rose plants of the new variety and shows the flowering thereof from bud to full bloom depicted in color as nearly correct as it is possible to make in a color illustration of the character. Throughout this specification, color values are based upon the Colour Chart of The Royal Horticultural Society of London, England, (1995 ed.) except where common terms of color definition are employed.

DESCRIPTION OF THE NEW VARIETY

The following description is of rose plants of the new cultivar grown outdoors in Wasco, Calif. in the month of October. Phenotypic expression may vary with environmental, cultural and climatic conditions, as well as differences in conditions of light and soil.

FLOWER

The new variety usually bears its flowers in clusters of three to four or more per stem. Flowers are borne in rounded to somewhat pyramidal clusters on strong long stems (about 34 to about 52 cms.). Outdoors, the plant blooms abundantly and nearly continuously during the growing season. The flowers have a slight spicy to rose fragrance.

BUD

The peduncle is about 2.2 to about 4.0 cms. in length, of slender to average caliper, usually erect but sometimes somewhat bending. It is moderately smooth, with many stipitate glands. Peduncle color is between 144B and 138B often moderately suffused especially on the side exposed to the sun with between 187B and 183B.

Before the calyx breaks, the bud is about 1.0 to about 1.5 cms. in diameter at the widest point, about 1.1 to about 1.6 cms. in length, and globular to somewhat ovoid in shape. The surface of the bud bears very few slender foliaceous appendages, few stipitate glands and some hairs, usually with slender entire foliaceous parts extending beyond the tip of the bud about ½ or more of its length. Bud color is between 144A and 138B often moderately suffused especially on the side exposed to the sun with between 187B and 183B.

The inner surface of the sepals is covered with fine wooly tomentum; sepal margins are lined with some stipitate glands and numerous hairs.

As the petals open (after the calyx breaks), the bud is about 1.2 to about 1.8 cms. in diameter at the widest point, about 1.2 to about 1.8 cms. in length, and globular to somewhat ovoid in form. The color of the under surfaces of the newly opened petals is between 60A and 53A. At the point where the petal attaches, there is a small zone of near 1D. The color of the upper surfaces of the newly open petals is between 187B and 53A. At the point where the petal attaches, there is a somewhat small zone of near 1D.

BLOOM

When fully open, the bloom ranges from about 5.8 to about 7.6 cms. in diameter. Petalage is very double with about 36 to 50 petals and about 5 to 7 petaloids arranged irregularly. When partially open, the bloom form is very cupped to globular, and the petals are moderately loose to cupped with petal edges somewhat reflexed outward. When fully open, the bloom form is more cupped and the petals are more loosely cupped to somewhat undulated with petal edges sometimes rolled to moderately reflexed outward.

PETALS

The substance of the petals is moderately heavy and of medium thickness with upper surfaces moderately velvety to satiny and under surfaces is moderately shiny. The outer petals are broadly obovate in shape with rounded apices. The inner petals are more narrowly obovate in shape with rounded apices. The petal margin is entire. Petals are about 2.1 to about 3.9 cms in length and about 1.8 to about 2.8 cms in width at the widest point.

NEWLY OPENED FLOWER

The under surface of the outer, intermediate and inner petals is between 60A and 53A. At the point where the petal attaches, there is a moderately small zone of near 1D.

The upper surface of the outer, intermediate and inner petals is between 53A and 53B. At the point where the petal attaches, there is a moderately small zone of near 1D.

The general tonality of the newly opened flower is between 53A and 53B.

THREE-DAY-OLD FLOWER

The under surface of the outer and inner petals is between 53B and 60B. At the point where the petal attaches, there is a moderately small zone of near 4D.

The upper surface of the outer and inner petals is between 53B and 60C. At the point where the petal attaches, there is a moderately small zone of near 4D.

The general tonality of the three-day-old flower is between 53B and 60C.

On the spent bloom, the petals usually drop off cleanly.

In October in Wasco, Calif., blooms on the bush growing outdoors generally last about four to five days. Cut roses from plants grown outdoors and kept at normal indoor living temperatures generally last about four to five or more days.

MALE REPRODUCTIVE ORGANS

Stamens are average in number (average about 65) and are arranged regularly about the pistils; a few are mixed with petaloids. The filaments are slender in caliper, most with anthers. Filaments are between 61C and 61B in color. The anthers open approximately at the same time. Anther color is between 16B and 19A when immature. Anther color at maturity is between 164B and 164A for the external part and near 200B for the internal part. Pollen is moderately abundant and near 11C in color. The filaments are about 0.5 to about 0.7 cm in length. The anthers are about 0.2 to about 0.3 cm in length. The styles are about 0.4 to about 0.7 cm in length.

FEMALE REPRODUCTIVE ORGANS

Pistils vary in number (average about 105). The styles are moderately uneven, moderately thin in caliper and somewhat loosely bunched. Stigma and style color is between 10C and 2C. Styles are sometimes lightly suffused with near 63A. Ovaries are usually all enclosed in the calyx.

Hips are somewhat short to average in length, moderately globular in form, and between 25A and 28B in color when ripe. The hip surface is very smooth with thick fleshy walls. There are approximately 10 to 16 seeds, medium in size.

FOLIAGE

The compound leaves are usually comprised of three to five or more leaflets and are borne abundantly. The five-leaflet leaves are about 7.2 to about 13.3 cms. in length and about 7.0 to about 10.2 cms. in width at the widest point, very heavy to leathery in texture and matte to slightly semi-glossy in finish. The terminal leaflets are about 3.6 to about 6.3 cms. in length and about 2.4 to about 3.8 cms. in width at the widest point, oval in shaped with moderately acute to somewhat acuminate apices and moderately round to somewhat acute bases. Their margins are usually simply serrate. The venation pattern of the leaf is pinnate and the vein color is between 138B and 147B.

The upper surface of the mature leaf is between 137A and 147A. The under surface of the mature leaf is between 138B and 147B. The upper and under surface of the young leaf is between 144A and 138A, often heavily suffused with between 183B and 187B.

The rachis is somewhat light to average in caliper and moderately rough. The upper side is somewhat shallowly grooved with many hairs and few stipitate glands on the edges of the grooves. The under side of the rachis is moderately rough with few very small prickles.

The stipules are about 1.2 to about 1.9 cms. in length and moderately wide with very long straight points that usually turn out at an angle of more than 90 degrees and sometimes recurve toward the stem.

The plant displays an above average degree of resistance to powdery mildew and rust as compared to other commercial varieties grown under comparable conditions in Wasco, Calif.

GROWTH

The plant has a spreading growth habit (with climbing canes about 250 to about 380 cms. in length). It displays very vigorous growth. Root initiation can vary between about 10 to 21 days. Temperature, age of the cutting wood and time of the year are variables. As indicated by the USDA plant hardiness zone map, the plants winter hardiness is between zones 5b and 6a. The plants drought/heat tolerance is yet to be determined. The diameter of the stems is about 1.5 to about 3.0 cms at the widest point. The sepals are about 5 in number, about 1.7 to about 2.8 cms in length and about 0.7 to about 1.0 cm in width at the widest point.

The color of the major stems is between 148A and 146B. They bear some medium-large prickles that are about 0.3 to about 0.7 cms. in length. The prickles are hooked moderately downward with a moderately short oval base; prickle color is between 165A and 166B. They bear no small prickles.

The color of the branches is between 146A and 138A. They bear many medium-large prickles which are of similar size and shape to the large prickles on the major stems; prickle color is between 164A and 165B. The branches bear few small prickles of similar shape and coloration.

The color of the new shoots is between 138A and 144A often moderately suffused with between 183B and 187B. They bear numerous prickles of variable size which are of similar shape to the medium-large prickles on the major stems; prickle color is between 183B and 187B.

I claim:

1. A new and distinct Climbing rose plant of the variety substantially as described and illustrated herein.

* * * * *

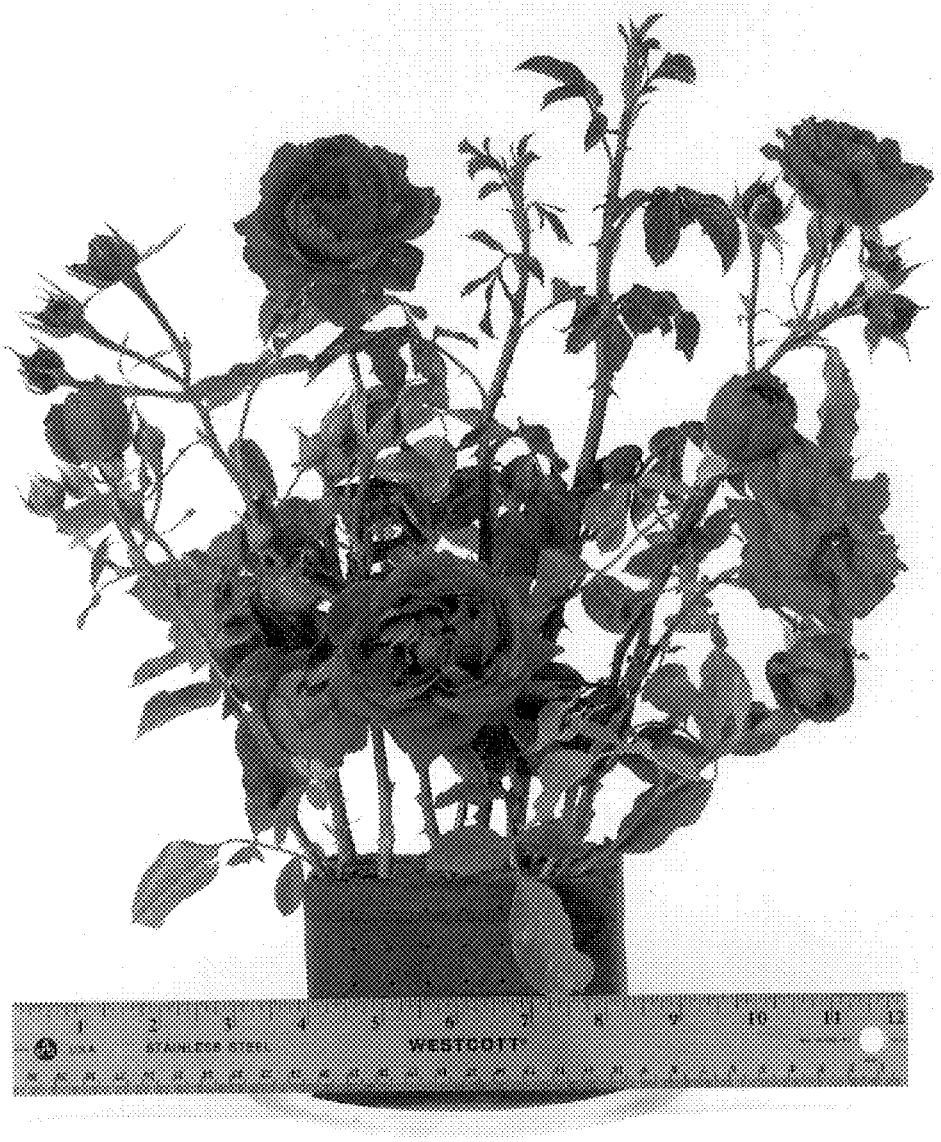
WESTCOTT